United States Patent [19]

Goto et al.

[11] Patent Number: 4,797,228

[45] Date of Patent: Jan. 10, 1989

[54] CYCLOHEXANE DERIVATIVE AND LIQUID CRYSTAL COMPOSITION CONTAINING SAME

[75] Inventors: Yasuyuki Goto, Yokohamashi; Shigeru Sugimori, Fujisawashi; Tetsuya Ogawa, Yokohamashi, all of Japan

[73] Assignee: Chisso Corporation, Osaka, Japan

[21] Appl. No.: 867,680

[22] Filed: May 28, 1986

[30] Foreign Application Priority Data

Jun. 10, 1985 [JP] Japan .............................. 60-125489

[51] Int. Cl.⁴ ..................... G02F 1/13; C09K 19/30; C07C 19/08; C07C 21/24; C07C 25/13
[52] U.S. Cl. ........................... 252/299.63; 252/299.5; 252/299.6; 350/350 R; 350/350 S; 570/129; 558/425
[58] Field of Search ............. 252/299.63, 299.5, 299.6; 558/425; 570/129; 350/350 R, 350 S

[56] References Cited

U.S. PATENT DOCUMENTS

| | | | |
|---|---|---|---|
| 4,261,651 | 4/1981 | Gray et al. | 252/299.63 |
| 4,400,293 | 8/1983 | Romer et al. | 252/299.63 |
| 4,419,263 | 12/1983 | Praefcke et al. | 252/299.63 |
| 4,439,015 | 2/1984 | Rich et al. | 252/299.63 |
| 4,455,443 | 6/1984 | Takatsu et al. | 252/299.63 |
| 4,482,472 | 11/1984 | Carr et al. | 252/299.63 |
| 4,510,069 | 4/1985 | Eidenschink et al. | 252/299.63 |
| 4,512,636 | 4/1985 | Andrews et al. | 252/299.61 |
| 4,514,044 | 4/1985 | Gunjima et al. | 252/299.63 |
| 4,551,280 | 11/1985 | Sasaki et al. | 252/299.63 |
| 4,556,745 | 12/1985 | Carr et al. | 252/299.63 |
| 4,602,851 | 7/1986 | Jenner et al. | 252/299.63 |
| 4,606,845 | 8/1986 | Romer et al. | 252/299.63 |
| 4,621,901 | 11/1986 | Petrzilka et al. | 252/299.63 |
| 4,630,896 | 12/1986 | Petrzilka et al. | 252/299.63 |
| 4,637,897 | 1/1987 | Kelly | 252/299.63 |
| 4,652,089 | 3/1987 | Oesterhelt et al. | 252/299.63 |
| 4,659,502 | 4/1987 | Fearon et al. | 252/299.63 |
| 4,695,131 | 9/1987 | Dalkwill et al. | 252/299.63 |
| 4,710,315 | 12/1987 | Schad et al. | 252/299.63 |
| 4,724,097 | 2/1988 | Romer et al. | 252/299.63 |

FOREIGN PATENT DOCUMENTS

| | | |
|---|---|---|
| 84194 | 7/1983 | European Pat. Off. ....... 252/299.63 |
| 107116 | 5/1984 | European Pat. Off. ....... 252/299.63 |
| 129177 | 12/1984 | European Pat. Off. ....... 252/299.63 |
| 149208 | 7/1985 | European Pat. Off. ....... 252/299.63 |
| 3410734 | 10/1985 | Fed. Rep. of Germany ........................ 252/299.63 |
| 3410733 | 10/1985 | Fed. Rep. of Germany ........................ 252/299.63 |
| 58-665 | 5/1983 | Japan .............................. 252/299.63 |
| 210057 | 12/1983 | Japan .............................. 252/299.63 |
| 80651 | 5/1984 | Japan .............................. 252/299.63 |
| 170042 | 9/1984 | Japan .............................. 252/299.63 |
| 193850 | 11/1984 | Japan .............................. 252/299.63 |
| 60-13731 | 1/1985 | Japan .............................. 252/299.63 |
| 45549 | 3/1985 | Japan .............................. 252/299.63 |
| 60-84230 | 5/1985 | Japan .............................. 252/299.63 |
| 8504874 | 11/1985 | PCT Int'l Appl. ............ 252/299.63 |
| 2121406 | 12/1980 | United Kingdom ........... 252/299.63 |
| 2092169 | 8/1982 | United Kingdom ........... 252/299.63 |
| 2134110 | 8/1984 | United Kingdom ........... 252/299.63 |

OTHER PUBLICATIONS

Kelly, S. M., et al., Helvetica, Chemica Acta., vol. 68, No. 5, pp. 1444–1452, (Aug. 14, 1985).

*Primary Examiner*—Teddy S. Gron
*Attorney, Agent, or Firm*—Wenderoth, Lind & Ponack

[57] ABSTRACT

A novel cyclohexane derivative having a good stability, a low viscosity and a large dielectric aniostropy value and a liquid crystal composition containing the same are provided, which derivative is expressed by the formula

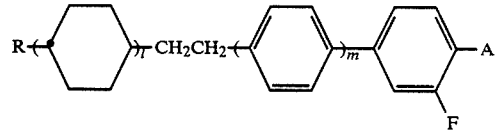

wherein R represents an alkyl group of 1 to 10 carbon atoms; A represents hydrogen, halogen or cyano group; l represents 1 or 2; and m represents 0 or 1.

5 Claims, No Drawings

CYCLOHEXANE DERIVATIVE AND LIQUID CRYSTAL COMPOSITION CONTAINING SAME

BACKGROUND OF THE INVENTION

1. Field of the Invention

This invention relates to a novel cyclohexane derivative and a liquid crystal composition containing the same.

2. Description of the Prior Art

Liquid crystal display elements utilize the optical anisotropy and the dielectric anisotropy of liquid crystal substances, and there are various modes such as those of T-N (twisted nematic) type, DS (dynamic scattering) type, guest-host type, DAP type, etc., depending on their display mode. The properties required for liquid crystal substances vary according to these modes, but it has been required in common that the substances exhibit liquid crystal phases within a temperature range as broad as possible and also they are stable to moisture, heat, light, air, etc.

At present, however, there is no single compound which satisfies all such requirements; hence liquid crystal compositions obtained by blending several kinds of liquid crystal compounds or blending these with compounds similar to liquid crystals have been used.

As examples of compounds having a 3,4-dihalogeneophenyl group or a 3-halogeno-4-cyanophenyl group, Japanese patent application laid-open Nos. Sho 58-83665/1983, Sho 58-210057/1983, Sho1 59-170042/1984, Sho 59-193850/1984, Sho 59-80651/1984 and Sho 60-45549/1985 disclose respectively ester compounds expressed by the following formulas (1)–(6):

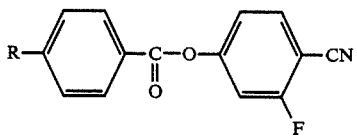 (1)

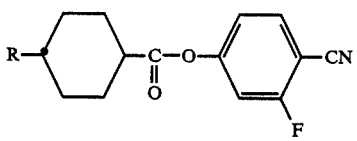 (2)

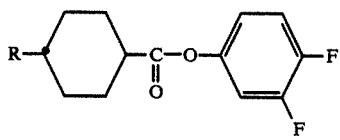 (3)

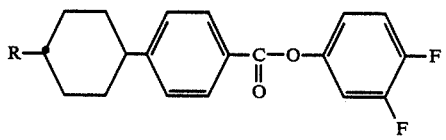 (4)

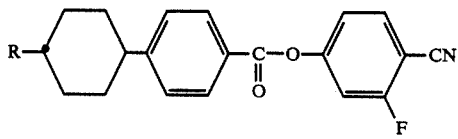 (5)

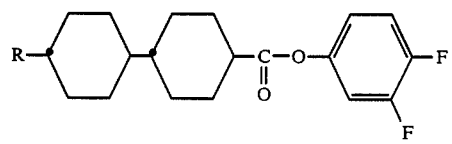 (6)

In the above formulas, R represents a linear chain alkyl group.

The compounds of the above formulas are liquid crystal compounds or compounds similar thereto, capable of being used as liquid crystal compositions by blending them with other liquid crystal compounds. The respective compounds of the above formulas, however, have drawbacks as described below. The compounds of the formulas (1), (2) and (3) constitute a liquid crystal blend having a relatively large dielectric anisotropy value ($\Delta\epsilon$), but the blend has a high viscosity, and further among these compounds, there are few which exhibit liquid crystal phases. Compounds expressed by the formulas (4), (5) and (6) have a relatively large dielectric anisotropy value and a suitable mesomorphic range, but they have a high viscosity.

Further, since the compounds (1)–(6) have an ester bond, they are liable to be hydrolyzed; thus liquid crystal compositions using these compounds could not have completely solved problems of stability, reliability, etc.

SUMMARY OF THE INVENTION

A first object of the present invention is to provide a compound which has a good stability, a low viscosity and a large dielectric anisotropy value, and also when it is used in admixture with other components to constitute a liquid crystal composition, has a good compatibility therewith and does not raise both the viscosity and the driving voltage of the liquid crystal composition together. A second object of the present invention is to provide a liquid crystal composition having a low viscosity and a low operating threshold voltage.

The present invention in a first aspect resides in a cyclohexane derivative expressed by the formula (I)

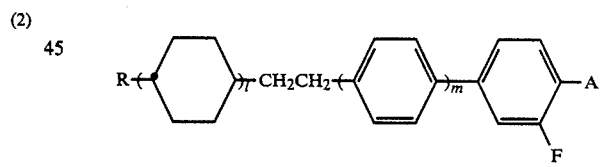

wherein R represents an alkyl group of 1 to 10 carbon atoms; A represents hydrogen, halogen or cyano group; l represents 1 or 2; and m represents 0 or 1.

The present invention in a second aspect resides in a liquid crystal composition having at least two components at least one of which is a cyclohexane derivative expressed by the formula (I) as set forth in the above first aspect of the present invention.

DETAILED DESCRIPTION OF PREFERRED EMBODIMENTS

The cyclohexane derivative of the present invention expressed by the formula (I) includes compounds expressed by the following formulas (a)–(h), as those which are preferred as a component of liquid crystal display materials, and in these formulas, R is as defined above and particularly preferred to be a linear alkyl group of 2 to 7 carbon atoms:

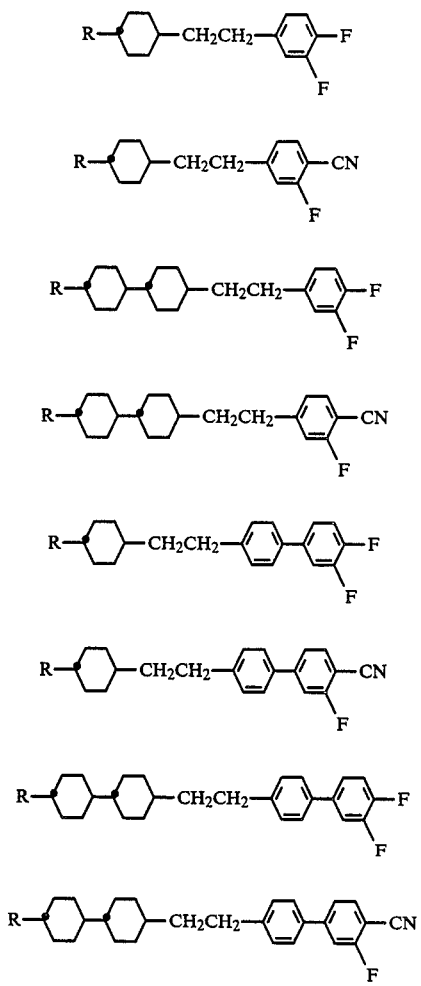

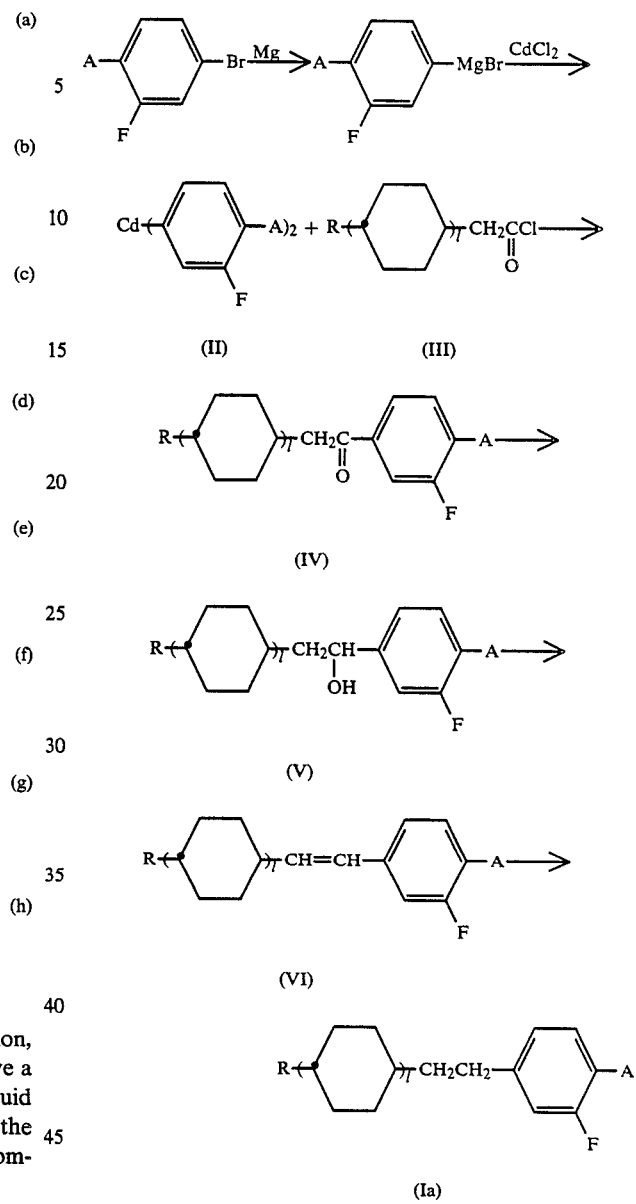

Among the compounds of the present invention, those of the formula (1) wherein $l=1$ and $m=0$ have a low viscosity and when used as a component of a liquid crystal composition, have a function of enhancing the dielectric anisotropy of the resulting liquid crystal composition.

In particular, the compounds expressed by the formulas (a) and (b) have an extremely low viscosity and a notable effectiveness upon its dielectric anisotropy.

By using such compounds having two 6-membered rings as a component of a liquid crystal material, it is possible to operate liquid crystal display elements at a low driving voltage.

Among the compounds of the present invention, compounds having three or four 6-membered rings have a broad mesomorphic range, and by adding these compounds as a component of a liquid crystal composition, it is possible to broaden the mesomorphic range of the resulting liquid crystal blend without raising the viscosity of the blend.

Next, a preparation example of the cyclohexane derivative of the present invention is illustrated below.

A compound (Ia) of the formula (I) wherein m represents zero and A represents hydrogen or halogen atom may be prepared according to the following scheme:

A Grignard reagent obtained by reacting a 3-fluoro-4-substituted-bromobenzene (or a 3-fluoro-bromobenzene) with metal magnesium is reacted with cadmium chloride to obtain a cadmium compound (II), followed by reacting this compound (II) with a substituted acetyl chloride expressed by the formula (III) to obtain a ketone derivative of the formula (IV). The reaction for obtaining this compound (IV) is preferred to be carried out at a temperature of 0°~150° C., preferably 60°~110° C. in an inert solvent such as benzene, toluene, etc. Successively the ketone derivative (IV) is subjected to reduction reaction in the presence of a suitable reducing agent such as lithium aluminum hydride, sodium borohydride, etc. to obtain an alcohol derivative (V), followed by subjecting this alcohol derivative to dehydration reaction in the presence of a catalyst described below in an inert organic solvent at a reflux temperature and under the atmospheric pressure to obtain an ethylene derivative (VI). As the inert organic solvent, benzene, toluene, chloroform, carbon tetrachloride, methylene chloride, etc. are suitable. As the catalyst for dehydration, Lewis acids such as aluminum chloride, tin tetrachloride, titanium tetrachloride, toluenesulfonic acid, etc., and mineral acids such as sulfuric acid, phosphoric acid, etc. may be used.

Successively the ethylene derivative (VI) is subjected to catalytic reduction reaction and the reaction mixture is subjected to a purification treatment suitable to the mixture, whereby it is possible to isolate the objective compound of the formula (Ia).

Further, a cyclohexane derivative (Ib) of the formula (I) wherein m represents zero and A represents -CN may be prepared for example as follows by a combination of known reactions:

Namely, the above compound of the formula (Ia) wherein A represents hydrogen is used as the starting raw material and this compound is subjected to Friedel-Crafts reaction to obtain a ketone compound of the formula (VII), followed by subjecting this compound to haloform reaction to obtain a carboxylic acid of the formula (VIII), chlorinating this compound into an acid chloride (IX), converting this chloride into an amide compound (X) and dehydrating it to obtain the objective compound (Ib).

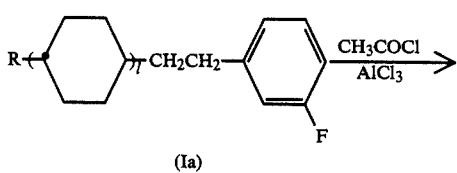

(Ia)

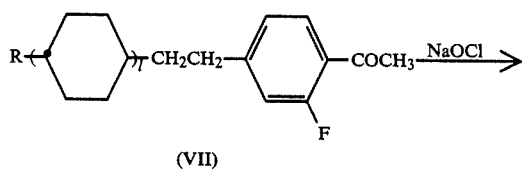

(VII)

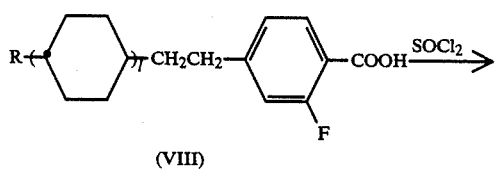

(VIII)

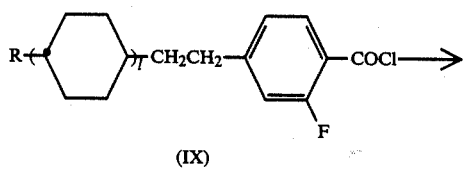

(IX)

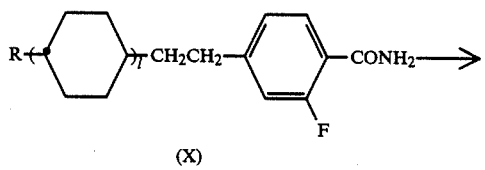

(X)

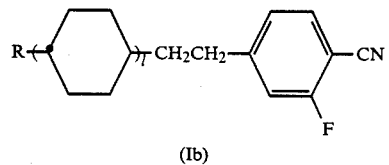

(Ib)

A comound (Ic) of the formula (I) wherein m represents 1 and A represents hydrogen or halogen atom may be obtained by subjecting the acid chloride of the formula (III) and a 3-fluoro-4-substituted biphenyl (XI) to Friedel-Crafts reaction to obtain a ketone derivative (XII) which is then reduced, dehydrated and hydrogenated.

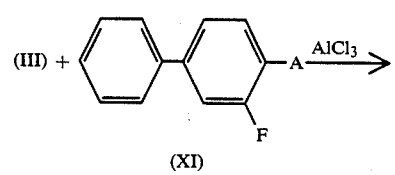

(XI)

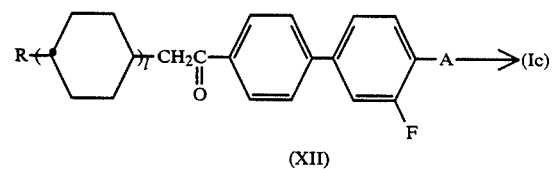

(XII)

A compound (Id) of the formula (I) wherein m represents 1 and A represents -CN may be obtained by cyanogenating the compound of the formula (Ic) wherein A represents Br by means of a cyanogenating agent such as cuprous cyanide.

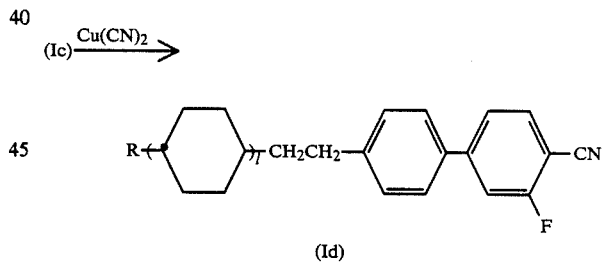

(Id)

The liquid crystal composition of the present invention contains the compound expressed by the formula (I) in a proportion of 0.1 to 99% by weight, preferably 1 to 40% by weight, more preferably 5 to 20% by weight.

As compounds which may be used in admixture with the compound of the formula (I), as a component of the liquid crystal composition of the present invention, a group of known compounds expressed by the following formulas (i)~(xxxiii) may be enumerated; in the above formulas (i)~(xxxiii), X represents

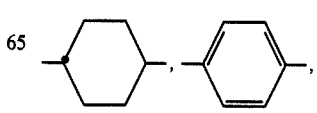

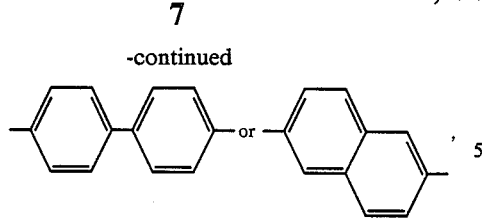
Y represents -CN, halogen, R' or -OR' and R and R' each represent an alkyl group:
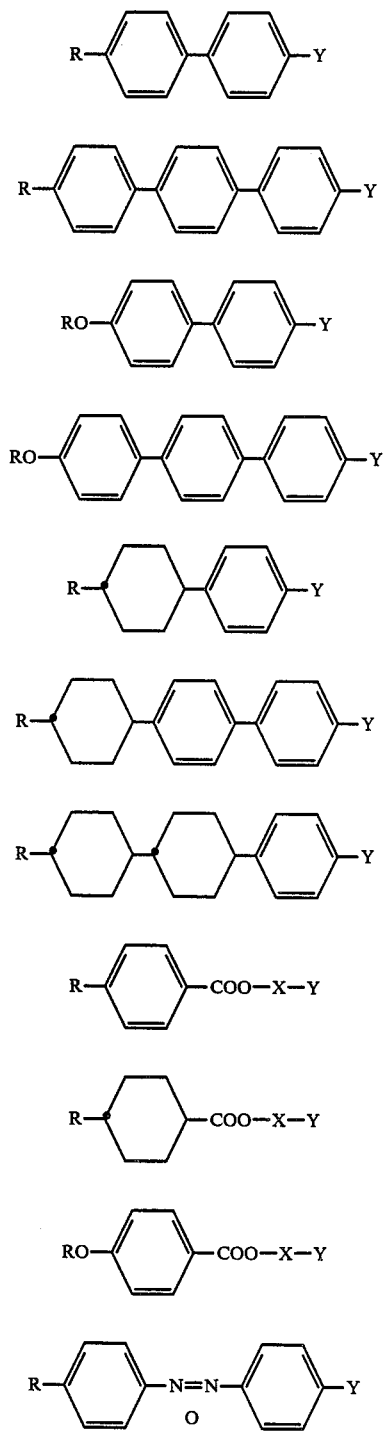
(i)
(ii)
(iii)
(iv)
(v)
(vi)
(vii)
(viii)
(ix)
(x)
(xi)
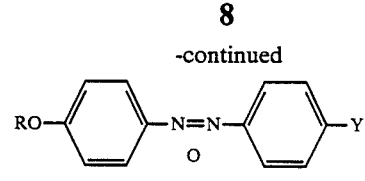 (xii)
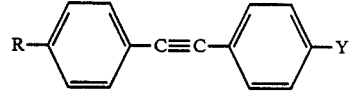 (xiii)
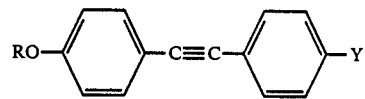 (xiv)
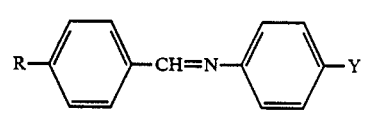 (xv)
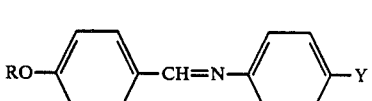 (xvi)
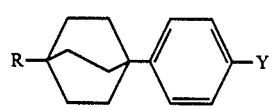 (xvii)
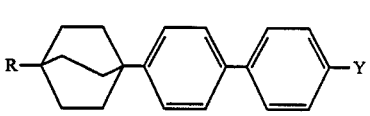 (xviii)
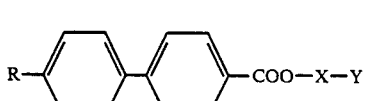 (xix)
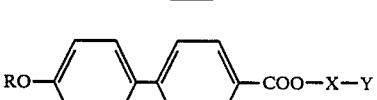 (xx)
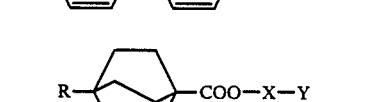 (xxi)
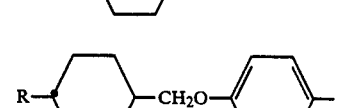 (xxii)
 (xxiii)
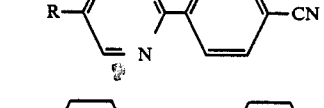 (xxiii)
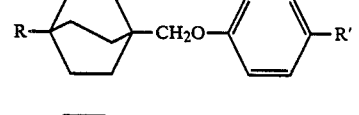 (xxiv)
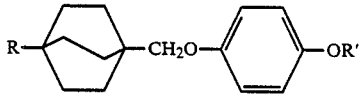 (xxv)

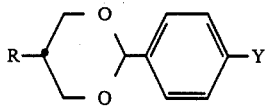  (xxvi)

  (xxvii)

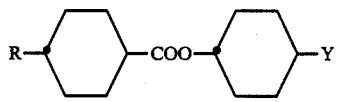  (xxviii)

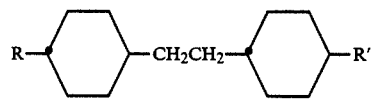  (xxix)

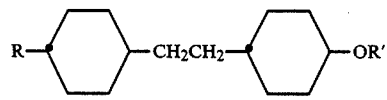  (xxx)

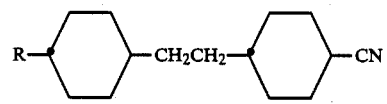  (xxxi)

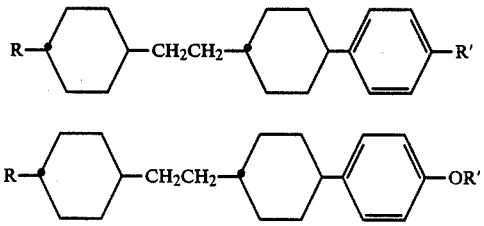  (xxxii)

(xxxiii)

The present invention will be described in more detail by way of the following Examples, but it should not be construed to be limited thereto.

In the Examples, the symbols C-I point, C-S point, S-N point, N-I point and S-I point mean crystallineisotropic liquid phase transition point, crystallinesmectic phase transition point, smectic-nematic phase transition point, nematic-isotropic liquid phase transition point and smectic-isotropic liquid phase transition point, respectively.

Further, the dielectric anisotropy values of liquid crystal compositions are abbreviated to Δε.

EXAMPLE 1

2-[Trans-4-(trans-4-propylcyclohexyl)cyclohexyl]-1-(3,4-difluorophenyl)ethane (i) Into a diethyl ether solution of a Grignard reagent prepared from 3,4-difluoro-1-bromobenzene (52.8 g, 0.274 mol) and magnesium (6.6 g, 0.274 mol) was added cadmium chloride (25.1 g, 0.137 mol), followed by refluxing the mixture for one hour, distilling off diethyl ether under reduced pressure, adding benzene (100 ml) to the resulting liquid, heating the mixture under reflux for one hour, adding a solution of trans-4-(trans-4-propylcyclohexyl)cyclohexylacetyl chloride (50.4 g, 0.177 mol) dissolved in benzene (100 ml), heating the reaction mixture under reflux for 2 hours, allowing it to cool down to room temperature, adding it to a mixed solution of water (500 ml) and sulfuric acid (20 g), separating the benzene layer, washing the benzene layer with water till the washing water became neutral, drying by means of anhydrous sodium sulfate, filtering off the drying agent, distilling off benzene from the benzene solution and recrystallizing a remaining oily substance from ethanol to obtain trans-4-(trans-4-propylcyclohexyl)cyclohexylacetyl-3,4-difluorobenzene (35 g). This product exhibited liquid crystal phases (C-I point: 98.2° C., N-I point 84.5° C.).

(ii) Next, a solution of the above trans-4-(trans-4-propylcyclohexyl)cyclohexylacetyl-3,4-difluorobenzene (13 g) dissolved in diethyl ether (50 ml) was added to a diethyl ether suspension (50 ml) of lithium aluminum hydride (1.2 g, 0.032 mol) at 0° C., followed by agitating the mixture at 0° C. for one hour, adding 20% sulfuric acid (50 ml) to the reaction material to dissolve the inorganic substance therein, extracting the separated oily substance with diethyl ether (100 ml), washing the separated ether solution with 10% sodium hydrogen carbonate solution and further with water till the washing water became neutral, drying the ether solution with anhydrous sodium sulfate, distilling off diethyl ether, adding to the remaining oily substance, p-toluenesulfonic acid (0.1 g) and toluene (50 ml), heating the mixture under reflux, removing the generated water to the outside of the system, allowing the resulting material to cool down to room temperature after completion of the reaction, washing the toluene solution with water till the washing water became neutral, drying the toluene solution with anhydrous sodium sulfate, distilling off toluene and recrystallizing remaining solids from ethanol to obtain 2-[trans-4-(trans-4-propylcyclohexyl)cyclohexyl]-1-(3,4-difluorophenyl)ethene (10.2 g). This product, too, exhibited liquid crystal phases (C-N point: 35.6° C., N-I point: 177.3° C.).

(iii) Next, the above 2-[trans-4-(trans-4-propylcyclohexyl)cyclohexyl]-1-(3,4-difluorophenyl)ethene (10 g) was dissolved in ethyl acetate (100 ml), followed by subjecting the solution to catalytic hydrogenation at 20° C. by means of 5%-Pd/C catalyst (0.5 g) till absorption of hydrogen ceased, removing the catalyst after completion of the reaction, distilling off ethyl acetate and recrystallizing a remaining oily substance from ethanol to obtain the objective 2-[trans-4-(trans-4-propylcyclohexyl)cyclohexyl]-1-(3,4-difluorophenyl)ethane (8 g). This product had a broad mesomorphic range, and C-S point: 18.4° C., S-N point: 49.5° C. and N-I point: 118.3° C.

EXAMPLE 2

The following compound was obtained in the same manner as in Example 1:

2-[trans-4-(trans-4-pentylcyclohexyl)cyclohexyl]1-(3,4-difluorophenyl)ethane

C-S point: 50.8° C., S-N point: 74.1° C., N-I point: 121.5° C.

In addition, compounds obtained as intermediates also exhibited liquid crystal phases. The phase transition points thereof are as follows:

trans-4-(trans-4-pentylcyclohexyl)cyclohexylacetyl-3,4-difluorobenzene

C-S point: 89.9° C., S-I point: 112.6° C.,

2-[trans-4-(trans-4-pentylcyclohexyl)cyclohexyl]1-(3,4-difluoro)ethene

C-N point: 47.1° C., N-I point: 178.5° C.

EXAMPLES 3~6

The following compounds were obtained in the same manner as in Example 1:

2-(trans-4-ethylcyclohexyl)-1-(3,4-difluorophenyl)ethane
C-I point: −35.1° C.

2-(trans-4-propylcyclohexyl)-1-(3,4-difluorophenyl)ethane
C-I point: −7.5° C.

2-(trans-4-butylcyclohexyl)-1-(3,4-difluorophenyl)ethane
C-I point: −0.5° C.

2-(trans-4-pentylcyclohexyl)-1-(3,4-difluorophenyl)ethane
C-I point: 1.5° C., N-I point: −30.1° C.

EXAMPLE 7

The following compounds were obtained in the same manner as in Example 1:

2-(trans-4-propylcyclohexyl)-1-(3,4-difluorobiphenylyl-4')ethane
C-N point: 64.1° C., N-I point: 88.7° C.

Compounds obtained as intermediates, too, exhibited liquid crystal phases. The phase transition points thereof are as follows:

4-(trans-4-propylcyclohexylacetyl)-3',4'-difluorobiphenyl
C-N point: 75.7° C., N-I point: 80.2° C.

2-(trans-4-propylcyclohexyl)-1-(3,4-difluorobiphenylyl-4')ethene
C-N point: 94.1° C., N-I point: 174.3° C.

EXAMPLE 8

2-[Trans-4-(trans-4-propylcyclohexyl)cyclohexyl]-1-(3-fluoro-4-cyanophenyl)ethane (i) 2-[Trans-4-(trans-4-propylcyclohexyl)cyclohexyl]-1-(3-fluorophenyl)ethane (50 g) obtained from 3-fluorobromobenzene and trans-4-(trans-4-propylcyclohexyl)and cyclohexylacetyl chloride in the same manner as in Example 1 was dissolved in nitrobenzene (100 ml), followed by adding anhydrous aluminum chloride (50.5 g) to the solution, agitating the mixture, dropwise adding acetyl chloride (29 g), reacting the mixture on heating at 40° C. on a water bath for 2 hours after completion of heat generation, adding the reaction mixture to a mixture of ice (500 g) and conc. hydrochloric acid (100 ml) to decompose the resulting aluminum chloride complex with vigorous stirring, extracting a liberated oily substance with toluene (200 ml), washing the extract liquid with water till the washing water became neutral, drying the toluene solution with anhydrous sodium sulfate, filtering off the drying agent, distilling off toluene and nitrobenzene under reduced pressure and recrystallizing the remaining oily substance from ethyl acetate to obtain 2-[trans-4-(trans-4-propylcyclohexyl)cyclohexyl]-1-(3-fluoro-4-acetyl)ethane (19 g). This product, too, exhibited liquid crystal phases (C-N point: 76.5° C., N-I point: 168.5° C.).

(ii) 2-[Trans-4-(trans-4-propylcyclohexyl)cyclohexyl]1-(3-fluoro-4-acetyl)ethane (10 g) obtained in the above paragraph (i) was dissolved in dioxane (100 ml), followed by adding to the solution, a solution of sodium hypobromite prepared from bromine (17 g) and sodium hydroxide (19 g), reacting the mixture on heating at 50° C. for 4 hours, allowing the reaction mixture to cool down after completion of the reaction, adding 6N hydrochloric acid (100 ml), filtering off a deposited bulk substance, drying it and recrystallizing from acetic acid (200 ml) to obtain 2-fluoro-4-{2-[trans-4-(trans-4-propylcyclohexyl)cyclohexyl]ethyl}benzoic acid (9.0 g). This product, too, exhibited liquid crystal phases (C-N point: 251.7° C., N-I point: >300° C.).

(iii) 2-Fluoro-4-{2-[trans-4-(trans-4-propylcyclohexyl)cyclohexyl]ethyl}benzoic acid obtained in the above paragraph (ii) was converted into the corresponding benzoyl chloride (5 g), which was then dissolved in dry toluene (10 ml), followed by adding the solution to a mixture of ice (100 g) and aqueous ammonia (30 ml), agitating the mixture vigorously, filtering off a deposited bulky substance, and drying it to obtain the corresponding benzamide (4.7 g). This product, too, exhibited liquid crystal phases (C-N point: 234.1° C., N-I point: 241.3° C.).

(iv) To the benzamide (4.7 g) obtained in the above paragraph (iii) were added toluene (50 ml) and thionyl chloride (50 ml) and the mixture was reacted on heating under reflux for 10 hours, allowing the resulting mixture to cool down after completion of the reaction, adding it in ice (100 g), agitating the mixture, separating the toluene layer, washing with 2N NaOH aqueous solution (50 ml), further washing with water till the washing water became neutral, drying over anhydrous sodium sulfate, removing the drying agent, distilling off toluene from the toluene solution and recrystallizing remaining solids from ethyl acetate to obtain the objective 2-[trans-4-(trans-4-propylcyclohexyl)cyclohexyl]-1-(3-fluoro-4-cyanophenyl)ethane (2.5 g). This product exhibited a broad liquid crystal range (C-N point: 72.1° C., N-I point: 172.9° C.).

EXAMPLES 9 AND 10

The following compounds were obtained in the same manner as in Example 8:

2-[trans-4-(trans-4-pentylcyclohexyl)cyclohexyl]1-(3-fluoro-4-cyanophenyl)ethane
C-N point: 66.4° C., (S-N point: 60.5° C.),
N-I point: 170.4° C.

2-[trans-4-propylcyclohexyl)-1-(3-fluoro-4-cyanophenyl)ethane
C-I point: 19.2° C., (N-I point: 7.2° C.)

EXAMPLE 11

A liquid crystal composition A consisting of
trans-4-propyl-(4-cyanophenyl)cyclohexane 30% by weight,
trans-4-pentyl-(4-cyanophenyl)cyclohexane 40% by weight and
trans-4-heptyl-(4-cyanophenyl)cyclohexane 30% by weight has a N-I point of 52.1° C., a dielectric anisotropy value Δε of 11.2 and a viscosity at 20° C. of 23.4 cp. This composition was sealed in a TN type cell of 10 μm thick and its characteristics at 20° C. were measured to give a threshold voltage of 1.54V and a saturation voltage of 2.13V.

To this liquid crystal composition A (85 parts by weight) was added 2-[trans-4-(trans-4-propylcyclohexyl)cyclohexyl]-1-(3,4-difluorophenyl)ethane (15 parts by weight) shown in Example 1. The resulting liquid crystal composition had a N-I point raised up to 60.2° C., a Δε of 12.1 and a viscosity at 20° C. lowered down to 22.0 cp, that is, it is seen that its effectiveness is superior. When this liquid crystal composition was sealed in the above TN type cell, the threshold voltage and the saturation voltage were 1.60V and 2.21V, respectively.

EXAMPLE 12

To the liquid crystal composition A (85 parts by weight) used in Example 11 was added 2-[trans-4-(trans-4-pentylcyclohexyl)cyclohexyl]-1-(3,4-difluorophenyl)-ethane (15 parts by weight) shown in Example 2. The resulting liquid crystal composition had a N-I point raised up to 60.1° C., a Δε of 11.8 and a viscosity at 20° C. lowered down to 21.8 cp. Further when this liquid crystal composition was sealed in the above TN cell, the threshold voltage and the saturation voltage were 1.57V and 2.14V, respectively.

EXAMPLE 13

To the liquid crystal composition A (85 parts by weight) used in Example 11 was added 2-[trans-4-(trans-4-propylcyclohexyl)cyclohexyl]-1-(3-fluoro-4-cyanophenyl)ethane (15 parts by weight) shown in Example 8. The resulting liquid crystal composition had a N-I point raised up to 68.0° C., a Δε somewhat raised up to 12.1 and a viscosity at 20° C. also somewhat raised up to 25.8 cp. When this liquid crystal composition was sealed in the above TN cell, the threshold voltage and the saturation voltage were 1.59V and 2.21V, respectively.

EXAMPLE 14

A liquid crystal composition B consisting of
trans-4-propyl-(4-cyanophenyl)cyclohexane 24% by weight,
trans-4-pentyl-(4-cyanophenyl)cyclohexane 36% by weight,
trans-4-heptyl-(4-cyanophenyl)cyclohexane 25% by weight, and
trans-4-pentyl-(4'-cyanobiphenylyl-4)cyclohexane 15% by weight
has a N-I point of 72.0° C., a dielectric anisotropy value Δε of 11.6 and a viscosity at 20° C. of 27.8 cp.

This composition was sealed in a TN type cell of 10 μm thick and its characteristics at 20° C. were measured to give a threshold voltage of 1.75V and a saturation voltage of 2.40V. To this liquid crystal composition B (85 parts by weight) was added 2-(trans-4-propylcyclohexyl)-1-(3-fluoro-4-cyanophenyl)ethane (15 parts by weight) shown in Example 10. The resulting liquid crystal composition had a N-I point of 62.5° C., a Δε of 13.7 and a viscosity at 20° C. lowered down to 26.4 cp. When this liquid crystal composition was sealed in the above TN cell, the threshold voltage and the saturation voltage were 1.50V and 2.07V respectively.

EXAMPLE 15

To the liquid crystal composition B (85 parts by weight) used in Example 14 was added 2-(trans-4-propylcyclohexyl)-1-(3,4-difluorophenyl)ethane (15 parts by weight) shown in Example 4. The resulting liquid crystal composition had a N-I point of 52.6° C., a Δε of 11.3 and a viscosity at 20° C. of 20.7 cp. When this liquid crystal composition was sealed in the above TN cell, the threshold voltage and the saturation voltage were 1.48V and 2.05V, respectively.

What we claim is:

1. A cyclohexane derivative expressed by the formula

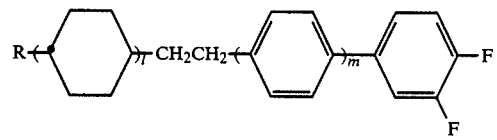

wherein R is an alkyl group of 1 to 10 carbon atoms; l is 1 or 2; m is 0 or 1; with the proviso that the sum of l and m is 1 or 2.

2. A cyclohexane derivative according to claim 1, expressed by the formula

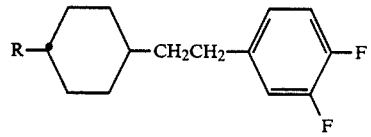

wherein R is as defined in claim 1.

3. A cyclohexane derivative according to claim 1 expressed by the formula

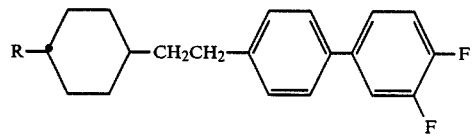

wherein R is as defined in claim 1.

4. A cyclohexane derivative according to claim 1 expressed by the formula

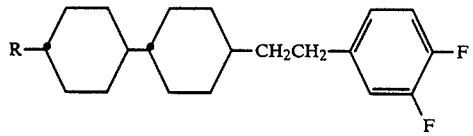

wherein R is as defined in claim 1

5. A liquid crystal composition having at least two components at least one of which is a cyclohexane derivative (I) as set forth in claim 1.

* * * * *

Adverse Decisions in Interference

Patent No. 4,797,228, Yasuyuki Goto. Shigeru Sugimori, Tetsuya Ogawa, CYCLOHEXANE DERIVATIVE AND LIQUID CRYSTAL COMPOSITION CONTAINING SAME, Interference No. 103,888, final judgment adverse to the patentees rendered December 22, 1997, as to claims 1, 2, 4 and 5.
*(Official Gazette April 21, 1998)*